United States Patent
Pfeuffer et al.

(10) Patent No.: US 6,769,145 B1
(45) Date of Patent: Aug. 3, 2004

(54) BEARING SURFACE FOR A MEDICAL EXAMINING-TABLE

(75) Inventors: Reinhard Pfeuffer, Elchesheim-Illingen (DE); Siegfried Röder, Ettlingen (DE); Isolde Licht, Bühl (DE); Heiko Bornheimer, Mannheim (DE); Bernhard Katzenstein, Sandweier (DE)

(73) Assignee: Maquet GmbH & Co. KG., Rastatt (DE)

(*) Notice: Subject to any disclaimer, the term of this patent is extended or adjusted under 35 U.S.C. 154(b) by 0 days.

(21) Appl. No.: 10/130,449

(22) PCT Filed: Nov. 16, 2000

(86) PCT No.: PCT/EP00/11394

§ 371 (c)(1),
(2), (4) Date: Sep. 10, 2002

(87) PCT Pub. No.: WO01/35828

PCT Pub. Date: May 25, 2001

(30) Foreign Application Priority Data

Nov. 16, 1999 (DE) .......... 199 55 119

(51) Int. Cl.⁷ .......... A61G 31/00
(52) U.S. Cl. .......... 5/601; 5/600; 378/209
(58) Field of Search .......... 5/600, 601, 81.1 HS; 378/208, 209; 600/415

(56) References Cited

U.S. PATENT DOCUMENTS 4,475,072 A * 10/1984 Schwehr et al. .......... 318/602
4,700,938 A * 10/1987 Chambron .......... 5/601

FOREIGN PATENT DOCUMENTS

| DE | 15 66 126 A | 12/1967 | |
| DE | 26 13 863 | 3/1976 | |
| EP | 0 899 026 A1 | 9/1997 | |
| EP | 000923922 A2 * | 6/1999 | A61G/13/02 |

* cited by examiner

Primary Examiner—Teri Pham Luu
Assistant Examiner—Fredrick Conley
(74) Attorney, Agent, or Firm—McCormick, Paulding & Huber LLP

(57) ABSTRACT

The invention relates to a bearing surface for a medical examining-table for carrying out roentgenolic examinations and surgical interventions during which radiological devices are used, comprising a table-top (16) and a guide unit (18) which can be coupled to a supporting column (14) of the examining table. Said guide unit has a first guide housing (20), in which the table-top (16) is guided to that it can be displaced in the longitudinal direction. The table-top consists entirely of X-ray permeable material and has guide surfaces (42,44), which lie against guide elements (38,40) in the guide housing (22).

14 Claims, 5 Drawing Sheets

BEARING SURFACE FOR A MEDICAL EXAMINING-TABLE

CROSS REFERENCE TO RELATED APPLICATIONS

Applicant hereby claims foreign priority benefits under 35 U.S.C. § 119 of German Patent Application No. 199 55 119.7 filed 16 Nov. 1999 and PCT Application No. PCT/EP00/11394, filed 16 Nov. 2000, the disclosure of which is herein incorporated by reference.

FIELD OF THE INVENTION

The invention concerns a support surface for a medical examination table for carrying out X-ray examinations and for carrying out surgical interventions with the intra-operation use of X-ray devices, including a table plate and a guide unit couplable with a support column of the examination table, the guide unit having a first guide housing in which the table plate is guided for movement in its longitudinal direction.

BACKGROUND OF THE INVENTION

Special examinations and surgical interventions (for example in vascular surgery) require a relative movement between the X-ray device and the investigation field, since the field can extend over a relatively large area, which is larger than the static image field of the X-ray device. An adjustment of the X-ray device is possible only to a limited extent, so that it is necessary to shift the support surface of the examination table with the patient. To make possible an unhindered use of the X-ray device, no disturbing obstructions may be located below the examination field. That means, that the support surface must extend far beyond the support column of the examination table.

SUMMARY OF THE INVENTION

Support surfaces of the aforementioned kind for X-ray examinations, for example with heart catheters, are known. In these support surfaces the table plates are however provided with metal rails which are guided in special guide elements of the guide unit for longitudinal movement of the table plate. These guide rails make themselves noticeable as shadows in the X-ray image, behind which no body structure of the patient is any longer recognizable. The area in which these guide rails are located is therefore not ray transmitting in an artifact free manner.

The length of the guide rails is determined by the size of the guide length which is necessary to react the resulting rotary moment produced by the weight of the patient, and by the stroke required for the longitudinal shifting. Accordingly the area of such a support surface which is not free for ray transmission in comparison to the size of the field to be examined is very large. The entire length of the support surface includes the length of the guide rails and the length of the fully ray transmissible "usable area", so that a large longitudinal extent of the system is obtained.

A support surface of the aforementioned kind is known from U.S. Pat. No. 4,700,938. The support surface described there consists of a foam material core and an outer shell of carbon fiber strengthened plastic. The outer shell consists of an upper portion, a lower portion and two C-profiles, which extend along the longitudinal edges of the table plate and at their C-legs are connected with the upper portion and the lower portion. The table plate lies on rollers which are supported in a support column. Two other track rollers are rotatably supported on the supporting column, each of which extends inwardly into a respective one of the C-profiles and lies on the lower C-leg of the C-profile, which together with the lower portion of the outer shell of the table plate forms a double layered edge strip. The upper C-legs of the C-profiles, together with a section of the upper portion of the outer shell above each tractor roll are drawn outwardly and bent downwardly somewhat so that these sections form a cover for the track rollers.

The present invention has as its object the provision of an at least longitudinally shiftable patient support surface of the above-mentioned kind, which together with having a short construction length has a large area for free transmission of X-rays and makes possible a large shifting movement in the longitudinal direction.

This object is solved in accordance with the invention by the features given in claim 1.

In the case of the support surface of the invention the non-ray transmitting area of the examination table is limited to the area of the guide unit, which is not accessible for the X-ray device, since it is located below the guide unit of the support column of the examination table. On the other hand, beyond the guide housing the table plate has a artifact free ray transmissibility, since it itself carries no metal parts which can influence the X-ray image. The lack of metallic guide rails or other guide elements is especially advantageous, if for optimal depiction of the examined organs the X-ray device is used with various projection mechanisms. The table plate can also transmit rays transmitted from the side or at an incline from below, without shadows of imaged metal parts hiding the body structure of the patient.

Preferably the table plate is made of carbon fiber reinforced plastic, since this material possesses the advantage of good X-ray transmissibility with at the same time high rigidity.

In a preferred embodiment, the table plate has two edge strips running in the longitudinal direction and a middle section substantially thicker in comparison to the edge strips. This middle section can be of trapezoidal form in a cross section perpendicular to its longitudinal direction, with the underside of the middle section being smaller than the upper side, so that the plate in its middle section tapers diminishingly towards its bottom. Because of the high thickness of the middle section the plate has a high load carrying capacity, with the inclinedly directed side surfaces of the table plate seeing to it that the bright to dark transition at the plate edge does not occur very abruptly in the X-ray picture.

Advantageously the guide elements are upper and lower support or guide rollers which simultaneously lie directly on upper and lower guide surfaces, respectively of the table plate. The upper and lower guide surfaces can in this case be formed on the two longitudinal edges of the table plate on the upper side and lower side respectively of the same. For example, the upper and lower guide surfaces can be formed on the previously mentioned edge strips at both sides of the middle section of the table plate.

The upper and lower guide rollers can be combined so as to be parts of a roller block wherein they are supported by a roller carrier, which carrier is pivotally supported on the guide housing for movement about an axis directed perpendicular to the longitudinal direction and parallel to the table plate, with at least two roller blocks being arranged on each longitudinal side of the table plate on the guide housing. By the provision of several rollers and the incorporation of the rollers into the roller blocks, one achieves a uniform distribution of the load on the rollers. The rollers consist preferably of plastic and to reduce the rolling resistance are preferably supported by roller bearings. By the pivotal support of the roller carriers each of the roller blocks in the case of a bending of the table plate can suit itself to the deformation of the edge strips of the table plate, so that a uniform distribution of the forces on all of the rollers is maintained. In a modified embodiment, the upper guide surfaces can be formed on the edge strips of the table plate, while on the under side of the middle section at least one lower guide surface is provided. This offers the possibility of supporting the middle section of the table plate by at least one guide roller engaging the under guide surface and extending over the entire width of the table plate.

The guide unit can have a second guide housing, on which are provided coupling and guide elements for coupling with the support column and for providing a lateral moment of the support surface relative to the support column. By a releasable connection between the guide unit and the support column support surfaces can be exchanged, and thereby special support surfaces for special examinations or operation disciplines can be used on the same pedestal. Additionally to the longitudinal and lateral shifting of the table plate the possibility can also be provided of adjusting the support surface in height and for inclining it in the longitudinal or lateral direction. Customarily the means for doing these adjustments are provided in the support column.

To avoid, in the case of an inclination of the support surface in the longitudinal direction, the appearance of an unintentional shifting of the support surface due to the resulting inclined drive force arising from the patient's weight, at least one brake unit is advantageously provided in the guide housing, which brake unit has brake elements, and a positioning mechanism for the brake elements, for engagement with surfaces of the table plate, for example with the upper and/or lower guide surface. Preferably brake units are arranged on both sides of the guide to achieve an increased braking effect, to create redundancy, and to avoid a non-uniform introduction of forces. The brake elements can be formed by two brake shoes which operate on the upper and lower sides of the edge strips of the table plate and which are released by an electromagnet. For safety purposes it is advantageous for the brakes to be active in the unenergized condition, that is for the brake shoes be held applied. The brake force in this case is created by a pre-stressed spring. For opening the brake the electromagnet is excited and releases the brake shoes against the spring force, so that a shifting of the support surface in the longitudinal direction can take place. To avoid that in the case of a bending of the support surface arising from the loading of the support surface a contact of the guide surfaces with the brake shoes occurs, the brake elements and the positioning mechanism are advantageously arranged on a brake carrier, which carrier is supported by means of rollers on an upper guide surface of the table plate and is secured against a movement in the longitudinal direction on the upper guide housing. The entire brake unit is therefore floatingly supported on the table plate by means of rollers and only in the longitudinal direction abuts against the frame of the first guide housing.

The shifting of the table plate can be achieved either manually or by motor. Before a shift the brakes must be first be released. This can be accomplished either by a foot switch or by a manually actuatable switch on the support surface. For safety reasons a release of the brakes should only be possible if the support surface is oriented horizontally, in order to avoid that if the support surface is longitudinally or laterally inclined an uncontrolled moment does not take place. In this case a control is therefore provided which in dependence on the angular position of the head of the support column, by means of which height adjustment, inclination in the longitudinal direction and tipping in the lateral direction is realized, enables or disables the actuation of the brake.

For motorized adjustment of the support surface at least one friction drive can be provided in the guide housing, which drive engages one edge strip of the table plate. The friction drive can for example include a drive roller coupled with a motor and two friction rollers, which friction rollers stand in permanent engagement with the drive roller and are in turn biased against a guide surface of the table plate. The motor is preferably an electric motor. With the inventive solution it is avoided that for reversing the rotational direction of the motor in a linear movement of the table plate, elements such as racks, threaded spindles or tension elements have to be used, which have the disadvantage that they for movement reversal have to lie partially in the ray path of the X-ray device in order to create a large stroke. Thereby shadows are created in the image field which make difficult the supervision in regard to the examination of the body structures. Moreover, since the friction rollers are moveably supported and are biased against the drive roll as well as against the guide path, wear can be equalized and deformation of the support surface by its loading can be taken into account.

For achieving a sufficiently large drive force one must increase the frictional value of the drive rollers by the choice of a suitable work material such as for example rubber or polyurethane. Since these materials have no especially large permissible surface pressure, the achievable pressing force and thereby also the friction force is limited by the given roller width. By the widening of the friction rollers the permissible pressing force for the frictional work material can be so far increased that the drive rollers can at the same time take on the function of supporting the gravity force applied by the plate onto the guide unit. The achievable drive force is in this case directly dependent on the loading of the rollers, which has the advantage that even in the case of a large patient weight and a large unloading of the support surface by way of the guide a sufficiently large drive force is created. By the combination of the two functions "guide" and "drive" there results also a simple construction of the longitudinal guiding for the support surface. This advantage especially allows the achievement of the above described solution, in which case the lower guide roller extends transversally across the entire width of the table plate, with this guide roller being connected with a drive motor.

In order to realize the desired shifting of the support surface in the lateral direction, the upper or first guide housing is by means of suitable guide elements shiftably arranged relative to the lower or second guide housing or relative to the supporting column. Therefore, for the required lateral shifting of the support surface it is not necessary to achieve ray transmissible guides since the lower guide housing is located in the region of the support column where no accessible possibility for the X-ray device exists. Therefore here known guide elements can be used. Since the support surface can also be laterally inclined or tilted it is advantageous to provide a brake unit for the lateral guides, in order to avoid an unintentional shifting of the table plate.

BRIEF DESCRIPTION OF THE DRAWINGS

Further features and advantages of the invention will be apparent from the following description, which in connection with the accompanying drawings explain the invention by way of exemplary embodiments. The drawings are.

DETAILED DESCRIPTION OF THE PREFERRED EMBODIMENTS

Figure 1:
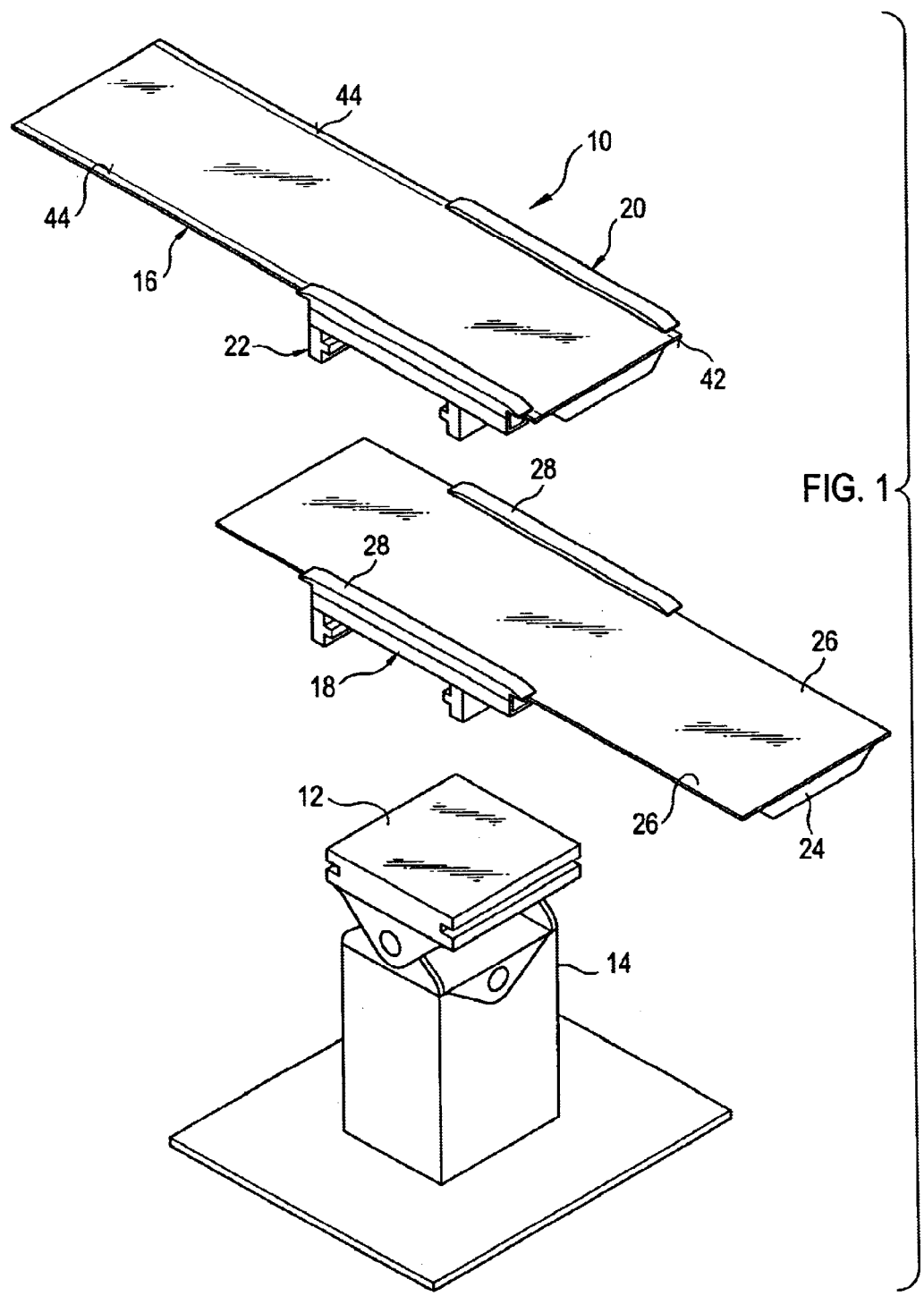
FIG. 1 a schematic perspective complete view of an examination table with the support surface of the invention shown in two different positions, FIG. 2 a schematic longitudinal section through a side rail of the upper guide housing, FIG. 3 an enlarged longitudinal section through a roller block of the guide alone, FIG. 4 a section transverse to the longitudinal direction through a side beam of the upper guide housing and the edge area of the table plate along line IV—IV in FIG. 2, FIG. 5 a schematic, partially cut away side view of a brake unit, FIG. 6 a schematic, partially broken away side view of a drive unit for a longitudinal shifting of the table plate, FIG. 7 a schematical side view of modified embodiment of the support surface of the invention with combined drive and guide rolls, and FIG. 8 a section transversed to the longitudinal direction through the second embodiment of the support plate of the invention along line VIII—VIII of FIG. 7.

FIG. 1 shows a complete view of a patient support surface 10 which is connectable to the head 12 of a support column 14 of an examining table. The support surface 10 consists of a table plate 16 and a guide unit 18, which includes an upper guide housing 20 and a lower guide housing 22. The table plate 16 is slidably guided in the upper guide housing 20 in its longitudinal direction, as is illustrated by the two positions of the table plate 16 in FIG. 1. The lower guide housing 20 is slidably guided on the head of support column 12 in a non-illustrated way, so that the support surface 10 in its entirely is shiftable perpendicularly to the longitudinal direction of the table plate 16.

The table plate 16 has a thick middle section 24 with a trapezoidal cross section and two thin edge strips 26 along its longitudinal sides. The table plate is entirely, and indeed therefore in the area between both of the edge strips 26, made without disturbing metal parts and therefore is artifact free in regard to penetration by rays. For example the table plate 16 is made of carbon fiber reinforced plastic.

Figure 2:
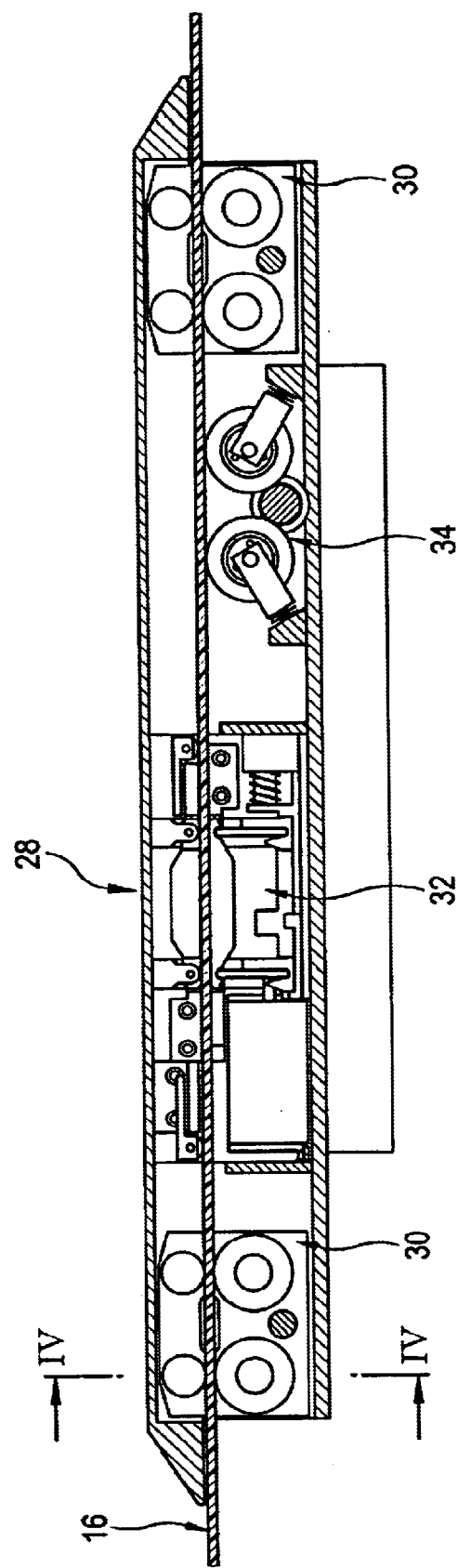

FIG. 2 shows a side beam 28 of the upper guide housing 20. At the ends of the side beam 28 are two roller blocks 30 which serve for guiding the table plate 16 in the longitudinal direction. Between the two roller blocks 60 a brake unit 32 is arranged on one side, which brake unit is freely shiftable perpendicularly to the plane of the table plate 16 and which in the longitudinal direction abuts the beam 28. Also between the two roller blocks 30 is a drive unit 34 for shifting the table plate 16.

Figure 3:
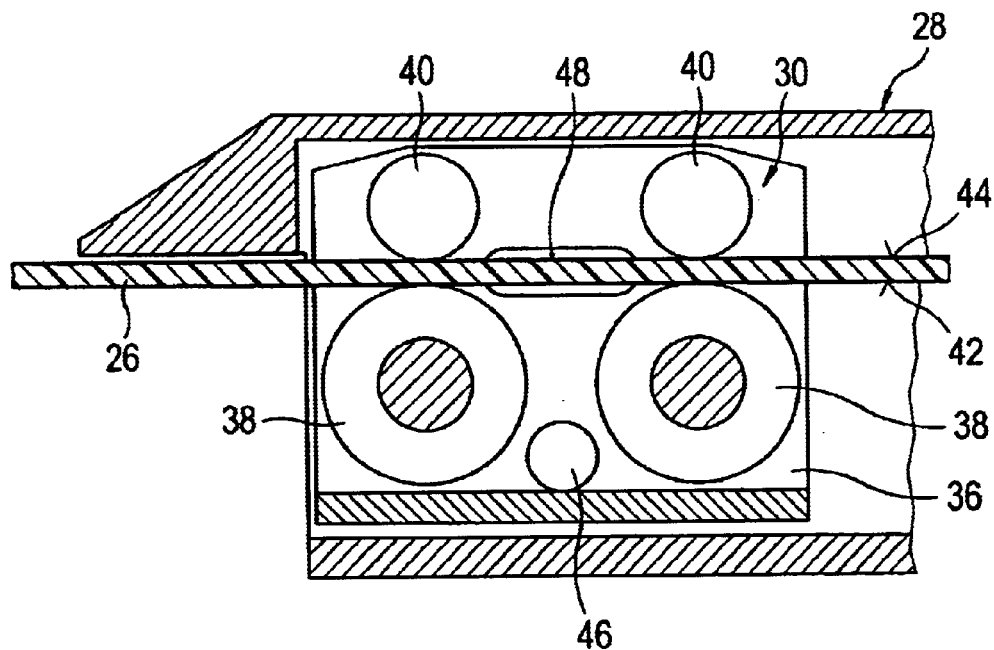
Figure 4:
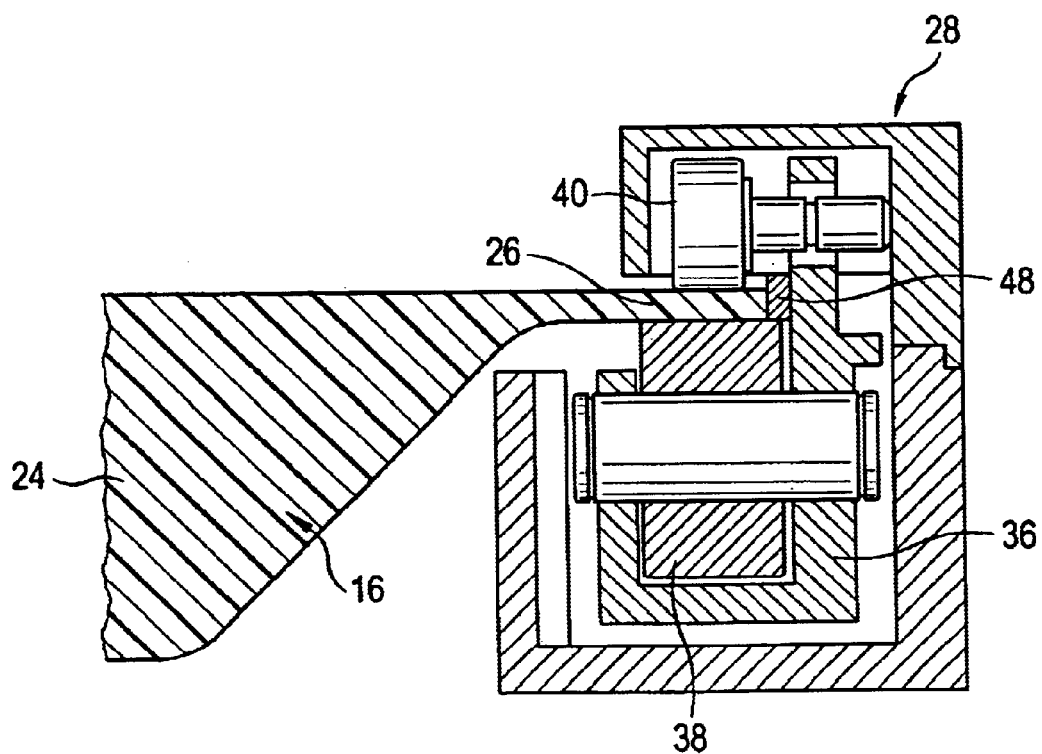

A roller block 30 is illustrated in more detail in FIGS. 3 and 4. The roller block consists of a roller carrier 36 in which are supported the lower support rollers 38 and upper support rollers 40. An edge strip 26 of the table plate 16 is positioned between the rollers 38 and 40, so that the lower rollers 38 and the upper rollers 40 run on a lower guide surface 42 or an upper surface 44, respectively, which are formed on the lower and upper side respectively of the edge strip 26. For realizing a uniform load distribution, the roller carrier 36 is supported on the side beam 28 for pivotal movement about an axis 46. During a longitudinal shifting of a the table plate 16, the rollers 38 and 40 roll on the edge strip 26 of the table plate 16. If the table plate bends because of the load, the roller block 30 adjusts itself by a pivotal movement about the axis 46 so that nearly similar forces are applied to the two roller pairs 38, 40. In this way the loading of the rollers is diminished as is also the loading of the upper surface of the table plate 16, which leads to a reduction in the abrasion of the table plate 16. For lateral guiding of the table plate 16 guide bars 48 are incorporated into the roller carrier 36, which guide bars 48 inhibit a lateral deflection of the table plate relative to the upper guide housing 20.

Figure 5:
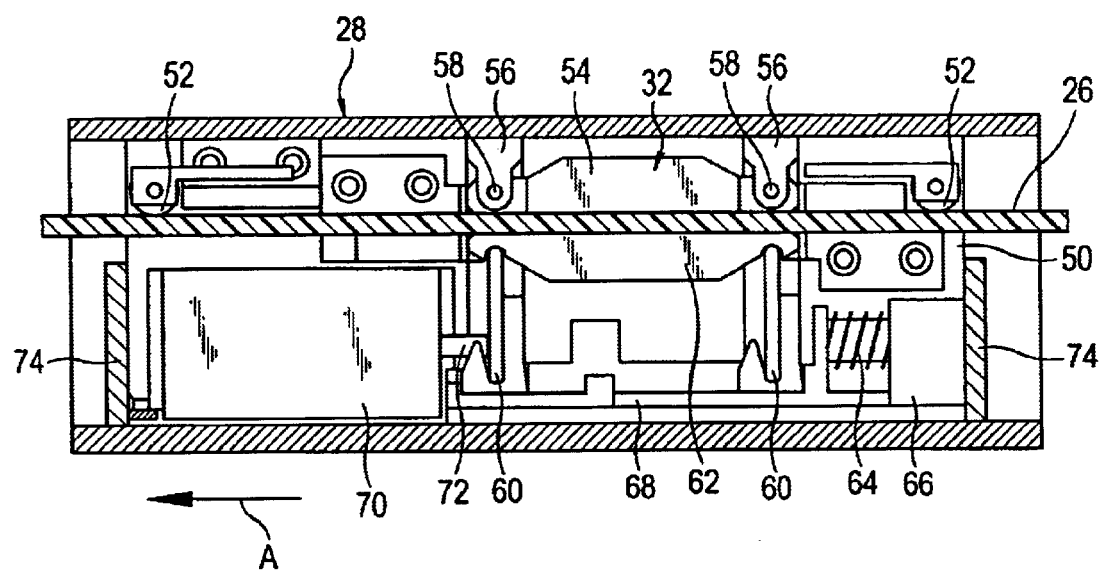

FIG. 5 shows the brake unit 32 in enlarged scale. The brake unit serves to avoid an unintentional movement of the table plate by way of external influences. The brake unit includes a frame 50 on which the rollers 52 are supported, by means of which rollers 52 the entire brake unit 32 runs on the edge strip 26 of the table plate 16, that is on the upper guide surface 44 of a edge strip 26. An upper brake shoe 54 is fastened to the frame 50. On the upper brake shoe 54 are two levers 56 each of which is pivotally supported for movement about an associated axis 58, which levers through further levers 60 carry a lower brake shoe 62. If the two levers 56 are pivoted about their axes 58, the distance between the two brake shoes 54 and 62 is changed. The pressing force for the brake shoes 54 and 62 is created through a spring 64, which at one side abuts against a part 66 fixed to the frame and its other side abuts against a movable slide 68, which in turn works on the lever 56 and biases the levers 56 in the direction of the arrow A in FIG. 5. The force of the spring 64 is amplified by the lever advantage of the lever.

An electromagnet 70 serves for opening the brake and is fastened to the frame 50, and with its armature 72 operates one of the levers 60. If the electromagnet is energized, the armature 72 moves in the direction opposite to the arrow A of FIG. 5. The magnetic force overcomes the force of the spring 64 so that the slide 62 is moved to the right in FIG. 5 and the brake is released. The actuation of the electromagnet 70 allows the table plate to be shifted, whereas in the non-activated condition of the electromagnet 70, the brake holds the table plate 16 stationary. Since because of the lever advantage for creating a large brake force, the relative stroke between the upper brake 54 and the lower brake shoe 62 is small and it must be avoided that in the case in of a bending of the table plate 16 the table plate does not rub on the brake shoes when the brake is released. For this reason the brake unit 32 is guided on the edge strip 26 of the table plate 16 by the rollers 52, so that the brake shoes 54 and 62 independently of the bending of the table plate always have the same spacing from the surfaces of the plate. In the longitudinal direction the brake unit 32 abuts intermediate walls 74 of the side beam 28.

Figure 6:
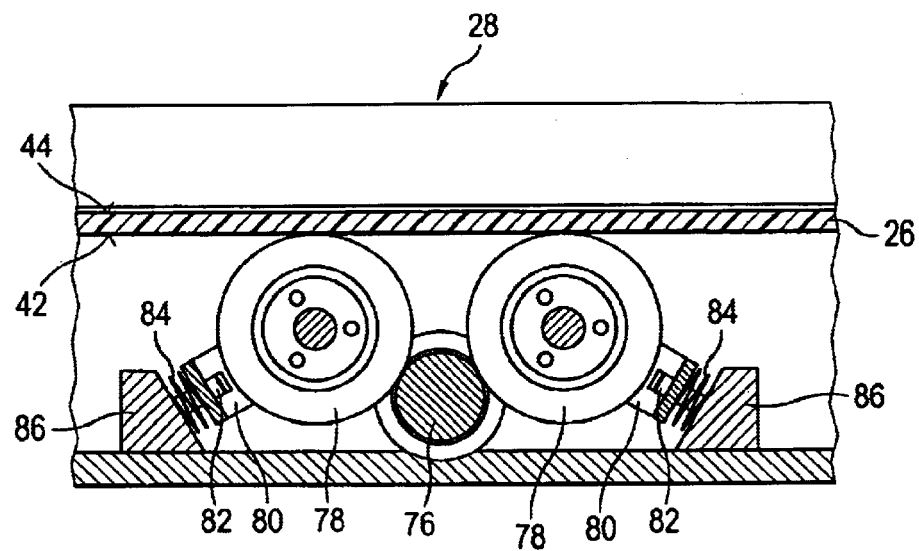

FIG. 6 shows the drive unit 34 which serves for shifting the table plate in its longitudinal direction. It includes a drive roller 76, which is driven by the a non-illustrated electric motor. The drive roller 76 stands in contact with two friction rollers 78, which are positioned at the under guide surface 42 of the one edge strip 26 of the table plate 16. The friction rollers 78 are each supported on a roller carrier 80 which is supported on a bolt 82 for free shifting movement within given limits, so that a change in the spacing between the drive roller 76 and the table plate 16 because of the loading of the support surface or because of rubbing due to the adjustability of the friction rollers 78 can be balanced. The required pressing force for the transmission of a moment by friction is in each case produced by a spring 84, which abuts a block 86 holding the bolt 82 and biases the friction roller 78 through the roller carrier 80 against the drive roll 76 on one hand and on the other hand against the lower guide surface of the edge strip 26.

The brake unit 32 and the drive unit 34 can be provided in only of the side beams 28 or in both of the side beams of the upper guide housing 20.

Figure 7:
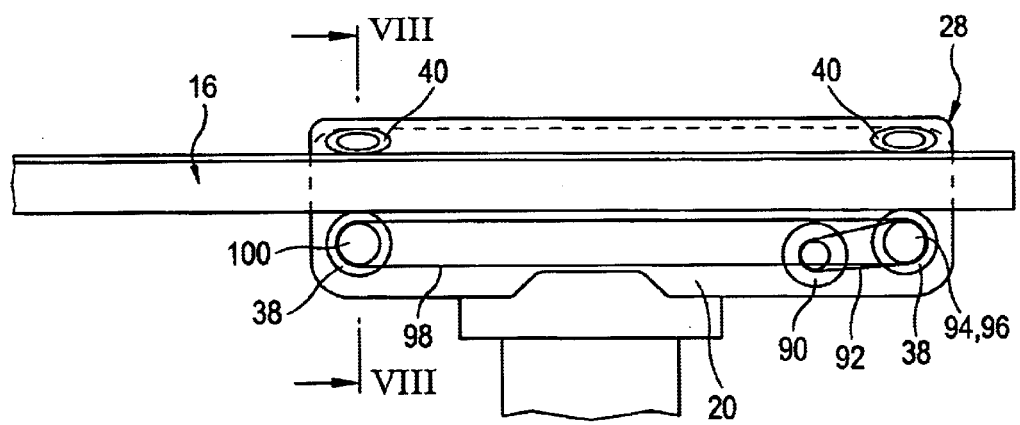
Figure 8:
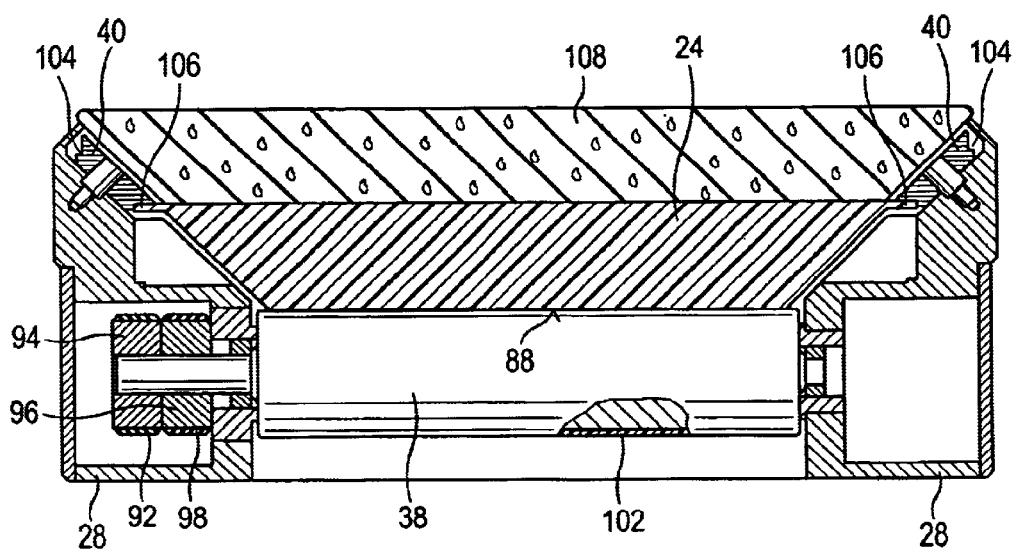

FIG. 7 and 8 show a second embodiment of the invention, wherein similar parts are provided with the same reference numerals. In the embodiment illustrated in FIGS. 7 and 8 the lower support rollers 38 extend over the entire width of the upper guide housing 20 and are supported in both of the side beams 28. The table plate 16 lies on the lower guide rolls 38 with the underside of its middle section 24 forming the lower guide surface 88. Thereby the surface pressure on the rollers as well on the table plate is reduced.

In the embodiment according FIGS. 7 and 8, the lower support rollers 38 at the same time serve to provide a drive for a shifting of the table plate 16. A motor 90, through a toothed belt 92 and a belt pulley 94, drives one of the support rollers 38. A second belt pulley 96 coaxial to the belt pulley 94 transmits the relative movement of the one support roll 38 by means of a toothed belt 98 and belt pulley 100 to the other support roller 38. It is thereby assured, that independently of the center of gravity of the table plate, with a patient lying on the table plate, a constant drive force is created. The lower support rollers 38 are coated with a layer 102 which has a high coefficient of friction, in order to create a sufficiently high drive force.

The upper support rollers 40, in the embodiment according to FIG. 8, are positioned inclinedly, in order to reduce the height of the side beams 28 and therewith also the entire height of the examination table. The rollers 40 are in this embodiment made as track rollers which have a circumferential groove 104 so that they do not lie on the upper guide surface 44 of the edge strips 26, but instead lie on the lateral edge surface 106 of the table plate 16. Thereby the rollers 40 in this embodiment in addition to opposing vertical forces also laterally guide the table plate 16.

In the embodiment according to FIG. 8 a cushion 108 is also illustrated on the table plate 16 which cushion improves the lying comfort of the patient.

What is claimed is:

1. A support surface for a medical examination table for carrying out X-ray examinations and surgical interventions with intra-operation use of X-ray devices, including a table plate (16), which consists entirely of X-ray transmitting material and has an upper and lower guide surfaces (42; 88) by means of which it lies on guide elements (38,40) making possible a shifting of the table plate relative to a support column (14), characterized in that the support surface (10) has a guide unit (18) with a guide housing (20) couplable with the support column (14) of the examination table, in which guide housing (20) the guide elements (38,40) are arranged and in which the table plate (16) is slidably guided in its longitudinal direction, and in that the table plate (16) has two edge strips (26) forming its longitudinal edges as well as a middle section (24) which is thicker than the edge strips (26), with at least the upper guide surfaces (44) being formed on the upper side of the edge strips (26).

2. A support surface according to claim 1 further characterized in that the middle section (24) has a trapezoidal shape in cross section perpendicular to its longitudinal direction, with the underside of the middle section (24) being smaller than its upper side.

3. A support surface according to claim 1, further characterized that the upper and lower guide surfaces (44,42) are formed along the two longitudinal edges (26) of the table plate (16) on the upper and lower sides respectively, of the table plate (16).

4. A support surface according to claim 1, further characterized in that the guide elements are upper and lower support or guide rollers (40, 38) which simultaneously directly engage the upper and lower guide surfaces (44, 42), respectively, of the table plate (16).

5. A support surface according to claim 4, further characterized in that several lower and upper guide rollers (38,40) are included in a roller block (30) and are supported on a roller carrier (36) which is pivotally supported on the guide housing (20) for movement about an axis of (46) perpendicular to the longitudinal direction and parallel to the table plate (16), with at least two roller blocks (30) being arranged on each longitudinal side of the support surface (10).

6. A support surface according to claim 1, further characterized in that at least one friction drive (32) engaging an end strip (26) of the table plate (16) is provided in the guide housing (20).

7. A support surface according to claim 6, further characterized in that the friction drive (32) includes a drive roller (76) coupled with a motor and two friction rollers (78) which in turn stand in permanent engagement with the drive roller (76) and on the other hand are biased against a guide surface (42) of the table plate (16).

8. A support surface according to claim 1 further characterized in that the upper guide surfaces (44) are formed on the edge strips (26) and in that the under side of the middle section forms at least one lower guide surface.

9. A support surface according to claim 8, further characterized in at the guide roller (38) which engages the at least one lower surface (88) extends perpendicularly over the entire width of the table plate (16).

10. A support surface according to claim 8 further characterized in that the upper guide rollers (40) are former as track rollers with a lateral guide (104) for the plate (16).

11. An apparatus according to claim 8, further characterized in that the lower guide rollers (38) are drive able by a motor (90).

12. A support surface according to claim 1, further characterized that in the guide housing (20) is arranged at least one brake unit (32) having brake elements (54, 62) for engagement with the surfaces (44, 42) of the table plate (16) and a positioning mechanism (64, 70) for the brake elements (54, 60).

13. A support surface according to claim 12, further characterized in that the brake elements (54, 62) and the positioning mechanism (64, 70) are arranged on a brake carrier (50), which brake carrier is supported by means of rollers (52) on an upper guide surface (44) of the table plate (16) and is secured against movement in the longitudinal direction of the table plate (16) relative to the first guide housing (20).

14. A support surface according to claim 1, further characterized in that the guide unit (18) has a second a guide housing (22) on which are provided coupling and guide elements for coupling with the support column (14) and for a lateral movement of the support surface (10) relative to the support column (14).

* * * * *